United States Patent [19]

Stahl et al.

[11] 4,395,489

[45] Jul. 26, 1983

[54] PROCESS FOR THE RECOVERY OF GLYCEROL DEHYDROGENASE

[75] Inventors: Peter Stahl, Bernried; Hans Seidel, Tutzing; Herwig Brunner, Weilheim, all of Fed. Rep. of Germany

[73] Assignee: Boehringer Mannheim GmbH, Mannheim-Waldhof, Fed. Rep. of Germany

[21] Appl. No.: 218,138

[22] Filed: Dec. 19, 1980

[30] Foreign Application Priority Data

Dec. 27, 1979 [DE] Fed. Rep. of Germany ....... 2952410

[51] Int. Cl.$^3$ .......................... C12N 9/04; C12R 1/01
[52] U.S. Cl. ..................................... 435/190; 435/828
[58] Field of Search ......................................... 435/190

[56] References Cited

U.S. PATENT DOCUMENTS 4,071,410  1/1978  Yoshizawa et al. ................ 435/218

FOREIGN PATENT DOCUMENTS 2021594  12/1979  United Kingdom ................ 435/190

OTHER PUBLICATIONS

Methods in Enzymology, vol. 19, pp. 113–140 (1970).
Advances in Enzymology, vol. 23, pp. 221–248 (1961).
Methods in Enzymology, vol. I, pp. 397–400 (1955).

*Primary Examiner*—Lionel M. Shapiro
*Attorney, Agent, or Firm*—Felfe & Lynch

[57] ABSTRACT

Process for obtaining high yields of glycerol dehydrogenase from micro-organisms and glycerol dehydrogenase having a low $K_M$ value.

14 Claims, No Drawings

PROCESS FOR THE RECOVERY OF GLYCEROL DEHYDROGENASE

This invention relates to a process for obtaining glycerol dehydrogenase from micro-organisms. In addition, the invention provides a new glycerol dehydrogenase which, relative to known glycerol dehydrogenases, has a substantially lower $K_M$ value.

Glycerol dehydrogenase is of particular importance for the determination of glycerol, the latter being liberated by the splitting of triglycerides. Therefore, the determination of glycerol with glycerol dehydrogenase (Glyc-DH) according to the equation:

$$\text{glycerol} + \text{NAD} \xrightarrow{\text{Glyc-DH}} \text{dihydroxyacetone} + \text{NADH}$$

in which NADH is measured by methods known for that purpose, plays an important role in the determination of triglycerides in which an equivalent amount of glycerol is first liberated from the triglyceride by lipase and possibly esterase.

A disadvantage of this process is that the glycerol dehydrogenase is obtained in relatively low yields in the case of the processes previously known for obtaining it and, due to the long period of fermentation necessary for the culturing of the micro-organisms, the expenses involved are too high. Thus, with the known processes, activity yields of only about 40 U/liter are achieved with culturing periods of about 24 hours.

Therefore, it is an object of the present invention to provide a process with which, in the case of the same or lesser expenditure, substantially higher amounts of the enzyme are obtained.

Thus, according to the present invention, there is provided a process for obtaining glycerol dehydrogenase from micro-organisms by culturing a glycerol dehydrogenase-forming micro-organism in an appropriate glycerol-containing nutrient medium, wherein the micro-organism is first cultured under aerobic conditions and thereafter under anaerobic conditions, i.e. with the exclusion of oxygen, whereafter the glycerol dehydrogenase formed is isolated from the biomass or from the nutrient medium.

The micro-organism used is preferably *Aerobacter aerogenes* DSM 1643 or NCIB 418.

We have found that with the micro-organisms used according to the present invention, at least 10 times better activity yields are obtained even without alteration of the other conditions. With the use of *Aerobacter aerogenes* DSM 1643, improved yields are even also obtained when using known processes for obtaining the enzyme in which culturing is carried out only aerobically or only anaerobically.

It is preferable to maintain the aerobic conditions, i.e. the supply of air or oxygen or oxygen-containing gases, up to the end of the log phase. By the log phase, there is to be understood the exponential or logarithmic growth phase, which is characterized by a constant, maximum partition rate.

It is known that glycerol dehydrogenase-forming micro-organisms usually best form this enzyme when they are cultured under anaerobic conditions, i.e. with the exclusion of oxygen. In most cases, in the presence of oxygen, a displacement of the metabolic performance occurs and, instead of glycerol dehydrogenase, glycerol-3-phosphate-dehydrogenase is formed and used for the decomposition of glycerol after previous phosphorylation with glycerokinase. However, micro-organisms have already been described which form glycerol dehydrogenase in the case of aeration (see Japanese Patent Specification No. 040737). In contradistinction thereto, we have now found that in the case of the above-described succession of aerobic and anaerobic conditions, substantially higher yields of enzyme can be achieved than in the case of a purely aerobic or anaerobic culturing. This is especially so in the case of the two above-mentioned micro-organisms.

Otherwise, the culturing of the micro-organisms and the recovery of the enzymes from the harvested micro-organisms take place by means of the methods known for this purpose. Thus, a known culture medium which can be used according to the present invention contains glycerol, peptone, meat extract, yeast extract and sodium chloride, as well as a buffer substance. The glycerol is thereby used as the sole source of carbon in relatively large amounts of about b 40 g./liter and used up in the course of the period of culturing which, in the case of the known processes, is about 24 hours. However, according to the present invention, we have found that even better results are achieved when, in the case of the aerobic/anaerobic method, the glycerol content is increased again in the anaerobic phase, i.e. more glycerol is added than is used up by the micro-organism. Therefore, the glycerol content is preferably adjusted in such a manner that, up to the end of the logarithmic growth phase, it has decreased to about 0.3 to 0.5% and, during the anaerobic phase, is again increased to 0.8 to 1.5%, i.e. to about the initial value.

Furthermore, it has proved to be advantageous to add biotin to the medium instead of yeast extract, the preferred biotin concentration being 10 to 100 µg./liter.

The culture temperature is within the usual limits, the temperature being kept at from 25° to 40° C. in order to achieve the desired flavorable results.

The pH value is preferably in the range of from 6 to 9, conventional buffer substances being used for the adjustment of the pH. Especially good results are obtained with the use of buffers containing phosphate and ammonium ions.

The process according to the present invention takes place substantially more quickly than the known processes. As a rule, optimum enzyme activity values are already achieved after a fermentation period of about 6 to 7 hours. The end of the culturing can easily be recognized by the commencement of a drop in the pH value.

When using the preferred conditions, it is possible, according to the present invention, to achieve enzyme activity yields of 9000 U/liter and above. This corresponds to a more than 100 fold increase in comparison with the known processes.

An advantageous peculiarity of the process according to the present invention is that, in the case of culturing *Aerobacter aerogenes* DSM 1643, a glycerol dehydrogenase is obtained which differs from the known glycerol dehydrogenases by having a substantially lower Michaelis constant $K_M$. Whereas in the case of the known enzymes, it is relatively large and is in the range of from 1 to $4 \times 10^{-2}$, the enzyme obtained according to the present invention from the above-mentioned strain has a $K_M$ value of $6.6 \times 10^{-4}$, i.e. is two powers of ten lower. Because of those advantageous properties, in the case of the use of this enzyme under otherwise the same conditions, a particular conversion rate is achieved with distinctly lower amounts of enzyme than in the case of the known glycerol dehydrogenases. Therefore, the present invention also provides a glycerol dehydrogenase with a $K_M$ of $6.6 \times 10^{-4}$.

As already mentioned, the desired enzyme can be obtained from the biomass of the micro-organisms by conventional methods. Thus, for example, the culture suspension can be directly digested by ultrasonic waves and, after separation of insoluble components, the enzyme can be isolated from the crude extract with conventional precipitation agents, for example ammonium sulphate. When using ammonium sulphate, it is preferable to fractionate at 35 to 45% saturation. A further enrichment can take place, for example, by a heating step, preferably for 2 to 10 minutes at 50° to 70° C. A part of the impurities is hereby denatured and can be removed by filtration or centrifuging. In this way, an enzyme is obtained with a specific activity of about 20 U/mg.

Culturing takes place in the usual manner by shake culturing or with stirring.

The following Examples are given for the purpose of illustrating the present invention:

EXAMPLE 1

*Aerobacter aerogenes* DSM 1643 is cultured in a medium which contains, by weight, 0.8% casein peptone, 0.8% meat peptone, 0.3% dipotassium hydrogen phosphate, 0.2% ammonium dihydrogen phosphate, 0.6% sodium chloride, 1 to 2% glycerol and 50 μg. biotin, at 37° C. and at a pH of 7.0, with aeration and stirring in a 10 liter fermenter. 300 liters of air per hour are introduced and stirring is carried out at 300 r.p.m. up to the end of the logarithmic growth phase.

At the end of the logarithmic growth phase, the supply of air is discontinued and the addition of glycerol commenced. The glycerol concentration thereby increases from 0.3 to 0.5% up to 1% at the end of the fermentation (about 6 hours). There is thus obtained a biomass of 7 to 10 g./liter and with an activity of 7000 to 9000 U/liter.

The culture suspension obtained is digested for 3 minutes in an ultrasonic device. Insoluble components are centrifuged off and the activity determination in the clear supernatent is carried out as follows:

Test solutions:

(1) Ammonium sulphate buffer solution:
Sodium bicarbonate (M.W.=84.01): 0.12 M=9.69 g./liter
ammonium sulphate (M.W.=132.15): 0.04 M=5.08 g./liter
adjust to pH 10.0 with 1 N sodium hydroxide solution.

(2) Nicotinamide-adenine-dinucleotide (NAD) solution
(M.W.=663.4) c=10 to 100, depending upon the crude extract sample used.

(3) 1.5 M glycerol
12.9 ml. 87% glycerol to 100 ml. double distilled water.

(4) Physiological sodium chloride solution (0.85% sodium chloride)
0.1 M phosphate buffer, pH 7.

| Test batch: | |
|---|---|
| measurement wavelength: | 366 nm |
| test volume: | 3.05 ml. |
| layer thickness: | 1 cm. |
| temperature: | 25° C. |

| Test batch: | |
|---|---|
| buffer/ammonium sulphate (1): | 2.65 ml. |
| NAD (2): | 0.10 ml. |
| sample: | 0.10 ml. |
| mix, await pre-running stage | |
| start with glycerol (3): | 0.20 ml. |
| Calculation: | $\frac{\Delta E \times 3.05 \times 1000}{3.4 \times 0.1 \times 1}$ = U/liter |

For the further purification of the enzyme, the crude extract is fractionated with an ammonium sulphate solution, the fraction with 35 to 45% saturation being collected and dissolved in 0.1 M phosphate buffer (pH 7) containing 0.85% sodium chloride. The solution is heated for 4 minutes at 60° C. and centrifuged. A clear solution of glycerol dehydrogenase is obtained with a specific activity of about 20 U/mg.

A $K_M$ determination with this preparation gives a value of $6.6 \times 10^{-4}$M.

EXAMPLE 2

The process of Example 1 was repeated, using *Aerobacter aerogenes* NCIB 418 (also known as *Enterobacter aerogenes*). The culture period is 8 hours and the crude extract has an activity of 3000 to 4000 U/liter.

It will be understood that the specification and examples are illustrative but not limitative of the present invention and that other embodiments within the spirit and scope of the invention will suggest themselves to those skilled in the art.

What is claimed is:

1. Process for obtaining glycerol dehydrogenase from micro-organisms, which process comprises culturing a glycerol dehydrogenase-forming *Aerobacter aerogenes* micro-organism in a glycerol-containing nutrient medium, culturing the micro-organism first under aerobic conditions, up to the end of the log phase, thereafter under anaerobic conditions, during which more glycerol is added to the nutrient medium than is used up by the micro-organism, and then isolating the glycerol dehydrogenase formed from the biomass or from the nutrient medium.

2. Process as claimed in claim 1 wherein the micro-organism is *Aerobacter aerogenes* DSM 1643.

3. Process as claimed in claim 1 wherein the micro-organism is *Aerobacter aerogenes* NCIB 418.

4. Process as claimed in claim 1 wherein the glycerol content of the nutrient medium in the anaerobic phase is increased from 0.3 to 0.5 up to 0.8 to 1.5%.

5. Process as claimed in claim 1 wherein the biotin is added to the nutrient medium.

6. Process as claimed in claim 1 wherein culturing is carried out at a temperature of from 25° to 40° C.

7. Process for obtaining glycerol dehydrogenase from micro-organisms, which process comprises culturing an *Aerobacter aerogenes* DSM 1643 in an appropriate glycerol-containing nutrient medium, and then isolating the glycerol dehydrogenase formed from the biomoass or from the nutrient medium.

8. Glycerol dehydrogenase with a $K_M$ value of $6.6 \times 10^{-4}$M.

9. Process for obtaining glycerol dehydrogenase from micro-organisms, which process comprises culturing a glycerol dehydrogenase-forming micro-organism selected from the group consisting of *Aerobacter aerogenes* DSM 1643 and NCIB 418 in a glycerol-containing nutrient medium, culturing the micro-organism first under aerobic conditions up to the end of the log phase and thereafter under anaerobic conditions and then isolating the glycerol dehydrogenase formed from the biomass or from the nutrient medium.

10. Process as claimed in claim 9 wherein more glycerol is added to the nutrient medium in the anaerobic culture phase than is used up by the micro-organism.

11. Process as claimed in claim 9 wherein the glycerol content of the nutrient medium in the anaerobic phase is increased from 0.3 to 0.5 up to 0.8 to 1.5%.

12. Process as claimed in claim 9 wherein biotin is added to the nutrient medium.

13. Process as claimed in claim 9 wherein culturing is carried out at a temperature of from 25° to 40° C.

14. Glycerol dehydrogenase according to the process of claim 7 and having a $K_M$ value of $6.6 \times 10^{-4} M$.

* * * * *